United States Patent
Schwartz et al.

(10) Patent No.: US 9,809,844 B2
(45) Date of Patent: *Nov. 7, 2017

(54) METHOD OF DNA ANALYSIS USING MICRO/NANOCHANNEL

(75) Inventors: David C. Schwartz, Madison, WI (US); Kyubong Jo, Champaign, IL (US); Dalia M. Dhingra, Arlington Heights, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 320 days.

This patent is subject to a terminal disclaimer.

(21) Appl. No.: 13/107,400

(22) Filed: May 13, 2011

(65) Prior Publication Data

US 2011/0275066 A1 Nov. 10, 2011

Related U.S. Application Data

(63) Continuation of application No. 11/633,232, filed on Nov. 29, 2006, now Pat. No. 7,960,105.

(60) Provisional application No. 60/740,583, filed on Nov. 29, 2005, provisional application No. 60/740,693, filed on Nov. 30, 2005.

(51) Int. Cl.
| | | |
|---|---|---|
| *B01L 3/00* | (2006.01) | |
| *C12Q 1/68* | (2006.01) | |
| *B82Y 15/00* | (2011.01) | |
| *B82Y 30/00* | (2011.01) | |

(52) U.S. Cl.
CPC ............ *C12Q 1/6837* (2013.01); *B82Y 15/00* (2013.01); *B82Y 30/00* (2013.01); *C12Q 1/6816* (2013.01); *C12Q 1/6869* (2013.01); *B01L 3/5027* (2013.01)

(58) Field of Classification Search
None
See application file for complete search history.

(56) References Cited

U.S. PATENT DOCUMENTS

| | | | | |
|---|---|---|---|---|
| 5,707,812 | A * | 1/1998 | Horn | C12Q 1/6806 435/252.3 |
| 6,117,634 | A * | 9/2000 | Langmore | C12Q 1/6853 435/6.11 |
| 6,150,089 | A * | 11/2000 | Schwartz | C12Q 1/68 204/450 |
| 6,294,064 | B1 * | 9/2001 | Reddy | G01N 27/44726 204/450 |
| 6,322,753 | B1 * | 11/2001 | Lindberg | B01L 3/502707 156/108 |
| 7,960,105 | B2 * | 6/2011 | Schwartz et al. | 435/6.1 |
| 2002/0187505 | A1 | 12/2002 | Stockton | |
| 2002/0187508 | A1 * | 12/2002 | Wong | C12Q 1/6825 435/5 |

OTHER PUBLICATIONS

"Base Pair," LIMSWiki.org, accessed Feb. 8, 2017.*
Roberts, Richard J., A nomenclature for restriction enzymes, DNA methyltransferases, homing endonucleases and their genes, Nucleic Acids Research 2003, vol. 31, No. 7, 1805-1812.

(Continued)

*Primary Examiner* — Joseph G. Dauner
(74) *Attorney, Agent, or Firm* — Quarles & Brady LLP

(57) ABSTRACT

Methods are provided for tagging, characterizing and sorting double-stranded biomolecules while maintaining the integrity of the biomolecules.

8 Claims, 5 Drawing Sheets

(56) References Cited

OTHER PUBLICATIONS

Samuelson, James C., The isolation of strand-specific nicking endonucleases from a randomized Sapl expression library, Nucleic Acids Research 2004, vol. 32, No. 12, 3661-3671.
Bousse L, et al., "Electrokinetically controlled microfluidic analysis systems," Annu. Rev. Biophys. Biomol. Struct. 29:155-181 (2000).
Heiter D, et al., "Site-specific DNA-nicking mutants of the heterodimeric restriction endonuclease R.BbvCI," J. Mol. Biol. 348:631-640 (2005).
Rye J, et al., "Stable fluorescent dye-DNA complexes in high sensitivity detection of protein-DNA interactions. Application to heat shock transcription factor," J. Biol. Chem. 268:25229-25238 (1993).
Wabuyele B, et al., "Single molecule detection of double-stranded DNA in poly(methylmethacrylate) and polycarbonate microfluidic devices," Electrophoresis 22:3939-3948 (2001).
Mukai, T. et al., "Isolation of circular DNA molecules from whole cellular DNA by use of APT-dependent deoxyribonuclease", 1973, Proc. Natl. Acad. Sci. USA, vol. 71, No. 10, pp. 2884-2887.
Trifonov, E.N., "Curved DNA", 1985, CRC Critical Reviews in Biochemistry, vol. 19, No. 2, pp. 89-106.
Garcia, H.G. et al., "Biological consequences of tightly bent DNA: The other life biological of a macromolecular celebrity", 2007, Biopolymers, vol. 85, No. 2, pp. 115-130.
Manning, G.S. "The persistence length of DNA is reached from the persistence length of its null isomer through an internal electrostatic stretching force." Biophysical Journal, 91:3607-3616.

* cited by examiner

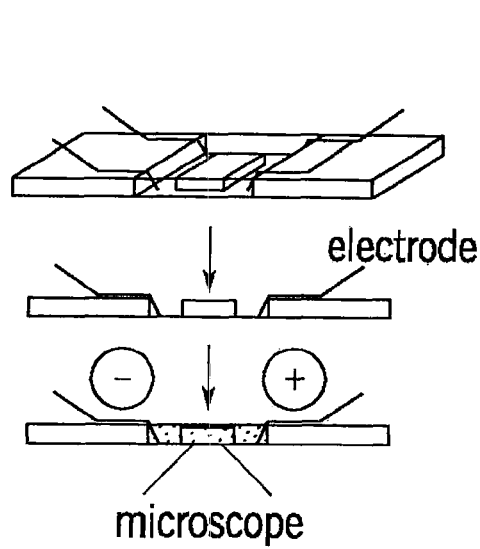
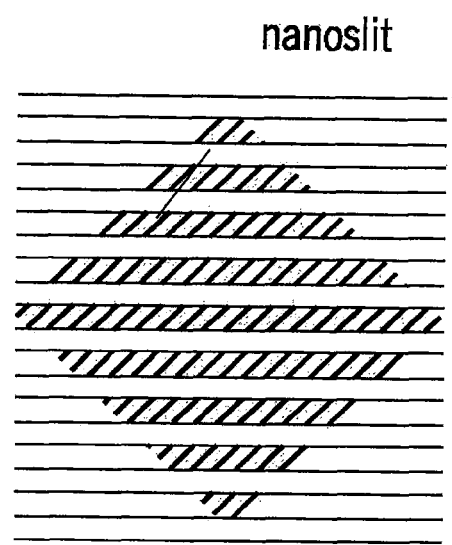
FIG. 5A
FIG. 5B

METHOD OF DNA ANALYSIS USING MICRO/NANOCHANNEL

CROSS-REFERENCE TO RELATED APPLICATIONS

This application is a continuation application of U.S. patent application Ser. No. 11/633,232, filed Nov. 29, 2006 now U.S. Pat. No. 7,960,105, which claimed the benefit of U.S. Provisional Patent Application Nos. 60/740,583, filed Nov. 29, 2005; and 60/740,693, filed Nov. 30, 2005. Each application is incorporated herein by reference as if set forth in its entirety.

STATEMENT REGARDING FEDERALLY SPONSORED RESEARCH OR DEVELOPMENT

This invention was made with government support under HG000225 awarded by the National Institutes of Health and 0425880 awarded by the National Science Foundation. The government has certain rights in the invention.

BACKGROUND OF THE INVENTION

The present invention relates to methods of presenting polymeric biomolecules such as nucleic acids for analysis, and in particular, to methods for tagging and elongating the biomolecules for characterization, sorting and analysis or other use.

A single DNA molecule can be elongated, for example, by shear forces of liquid flow, by capillary action or by convective flow, and then fixed in an elongated form to a substrate by electrostatic attraction. Sequence features of the fixed molecule can be identified by cleaving the fixed molecule with one or more restriction enzymes to produce gaps that can be marked by fluoroscopic markers or the like and then visualized. See, e.g., U.S. Pat. Nos. 6,713,263; 6,610,256; 6,607,888; 6,509,158; 6,448,012; 6,340,567; 6,294,136; 6,221,592. See also, U.S. Published Patent Application Nos. 2005/0082204; 2003/0124611; 2003/0036067. Each patent and published patent application is incorporated herein by reference as if set forth in its entirety. Although fixing the DNA to the substrate simplifies the analysis by preserving the elongated state, stabilizing the position of the molecule, and preventing fragment shuffling after cleavage, it is difficult to control chemical interactions with the DNA because of its close proximity to the substrate. Also, cleaved DNA may not be not suited for subsequent use, especially where fragment shuffling diminishes information content that can be obtained from an uncleaved molecule.

One can avoid such surface effects by suspending the DNA molecule in a "nanochannel" without attachment to the channel walls. A nanochannel is a channel having a cross-sectional dimension less than 1,000 nanometers and typically on the order of 30 nanometers. The suspended DNA molecule is sufficiently spaced apart from the channel walls to avoid surface interference in the reaction process while still stabilizing the DNA molecule sufficiently for analytical techniques.

Practical use of nanochannels faces a number of obstacles. Nanochannels are extremely difficult to fabricate, thus costly, and as a practical matter, are not reusable. In addition, the small size of nanochannels makes the addition of chemical reagents, especially enzymes, difficult. It is also difficult to encourage DNA molecules to enter the small cross-sectional area of nanochannels. Likewise, it can be difficult to remove interfering reaction by-products from nanochannels. Finally, because DNA is not under significant tension within nanochannels, restriction enzymes cutting the DNA may not make visible gaps.

SUMMARY OF THE INVENTION

The present invention provides methods for marking individual double-stranded polymeric nucleic acid molecules to yield intact, marked polymeric nucleic acid molecules suitable for characterization and for subsequent uses. In accord with the method, a single strand of the double stranded molecule is broken (nicked) but the integrity of the molecule is maintained. Because the molecule is not cleaved in the nicking process, the nicking process can be performed before the molecule is immobilized for analysis in a nanochannel, and optionally characterized and sorted for subsequent uses, including use in an array of sorted molecules.

The invention also relates to methods for providing the nicked, polymeric nucleic acid molecules in a low ionic strength buffer to increase the stiffness of the molecules, thereby facilitating use of devices having convenient geometries for characterization.

The third technique, rendered possible by the increased stiffness, is to use a channel having a nanometer scale in height, but a micrometer scale in width, relying on the greater stiffness of the elongated DNA molecule to remain properly aligned within the larger channels. The larger channel simplifies loading of the DNA, the introduction of reagents, and greatly simplifies channel construction, thereby reducing costs and making disposable channels practical.

These simplified processes for preparing the individual DNA molecules (which can include multiple copies of particular individual molecules, where, e.g., multiple genome-equivalents are analyzed) away from a surface and before introduction into the nanochannel, also simplify marking of the DNA molecule with multiple fluoroscopic materials. The use of fluorescence resonance energy transfer (FRET), in which one fluorescent material produces light exciting the other, allows dual color imaging and reduces the effects of unincorporated dyes because of the limited range of this effect. The profile of fluorescent labels on each imaged molecule, referred to as its 'barcode,' is characteristic of that molecule. From the characteristic barcode, the location of the molecule can be ascertained from an existing database of nucleic acid sequences of the source organism, tissue or cell type, in a manner known to the art. Individual molecules of interest can be flagged according to a user-specified set of parameters for further collection, analysis or other use.

In another aspect, the invention relates to sorting of nucleic acids characterized in accord with the invention. In particular, a nucleic acid molecule characterized in a nanochannel after site-specific labeling on a single strand as described elsewhere herein can be captured by, e.g., electrostatic attraction, to an electrode activated to capture on the particular molecule (or, e.g., a related class of molecules). The electrode can be provided in a microchannel (i.e., a channel having width and height dimensions greater than those of a nanochannel, e.g., 5 microns in width and 10 microns in height) in electrical connection with and under the logical control of a controller (such as a computer having a suitable user interface for specifying user parameters) that can also coordinate the process of matching the labeled nucleic acids against a genomic sequence database to identify and distinguish nucleic acid molecules of higher interest from those of lesser interest. In turn, the controller can address the electrode independently, thereby facilitating separate collection of one or more molecules at defined positions in an array. A plurality of electrodes, each under separate or coordinated control of one or more controllers, can effectively capture and accumulate a plurality of identical, related or distinct molecules characterized as described. Electrodes can be provided in a matrix suited for electrophoretic migration of nucleic acids, e.g., agarose or polyacrylamide, such that captured molecules tend to remain at or near the electrode until directed by the controller to release the captured molecules. Alternatively or additionally, a ligand can be provided at the capture site to fixedly or releasably retain the captured molecules at the site. A suitable capture system can be based upon the addressable electrode arrays described in various patents assigned to Nanogen, Inc., such as U.S. Pat. Nos. 7,101,717; 7,045,097; and 6,867,048, each of which is incorporated herein by reference as if set forth in its entirety. Other systems for capturing and/or releasing nucleic acid can be envisioned.

After capture on one or a plurality of such electrodes, identical or related captured molecules can be released from the electrodes in an ordered manner by reversing charge on the electrodes. Again, the release can be separately or coordinately controlled by the controller or controllers. Upon release, the molecules can be conveyed for subsequent analysis, such as sequencing analysis. The powerful labeling and identification features of the invention, coupled with the ability to selectively capture or discard identified molecules, yield a system for high-throughput analysis of nucleic acid molecules. One appropriate use for such released molecule(s) is a conventional nucleotide-level sequence analysis of the molecules to ascertain whether the obtained molecule(s) are identical to or different from a reference sequence in a pre-existing database. In a related embodiment, after the profile of each molecule is determined in a nanochannel and its value assessed, the molecule flows in a stream from the nanochannel into a sorting microchannel-sized chamber whereupon the controller instructs a microvalve in the chamber either (1) to open to reject a molecule of low interest from the chamber into a waste chamber or (2) to close so that a molecule of high interest is drawn (e.g., by charge) into a downstream system, such as a sequencing platform or amplification system. It will be understood that high throughput can be achieved in any of these embodiments by providing a plurality of nanochannels for sorting multiple molecules in parallel from a single inlet source along with a controller network and software having adequate facility to manage the parallel sorting and disposition of the tagged molecules.

These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The invention will be better understood and features, aspects and advantages other than those set forth above will become apparent when consideration is given to the following detailed description thereof. Such detailed description makes reference to the following drawings, wherein:

FIGS. 5a and b depicts a design of a suitable micro-nanochannel device.

DETAILED DESCRIPTION OF PREFERRED EMBODIMENTS

The present invention relates to the observation that when large genomic DNA molecules are a primary analyte, a key issue becomes how to unravel and mark DNA molecules for high-throughput application. With respect to unraveling DNA molecules, high-throughput methods and systems using nanochannels for analyzing single, intact DNA molecules are possible at low buffer ionic strength because persistence length of DNA molecules inversely varies with ionic strength of a buffer. Likewise, and with respect to marking of DNA molecules, labeled, sequence-specific nucleotides can be added to DNA molecules nicked at specific sites using endonucleases that do not catalyze double strand cleavage of the molecules, thereby providing markers of site-specific nicking. Using available genomic sequence information, one can correlate the site-specific markers with identifiable nucleic acid molecules. Desired nucleic acid molecules so identified can be sorted and collected for subsequent use. It will be appreciated that intact individual nucleic acid molecules prepared for presentation and analysis as described herein can alternatively be analyzed after being deposited on a surface, with the understanding that difficulty in removing such deposited molecules precludes subsequent analysis of such molecules, e.g. by nucleic acid sequencing or other methods.

Figure 1:
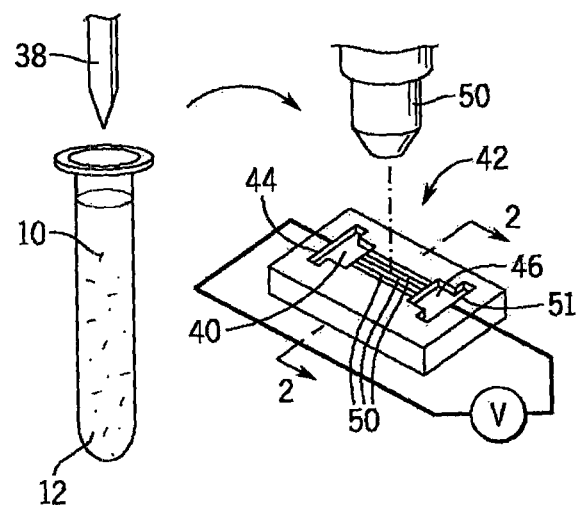
FIG. 1 is a graphical representation of the process of the present invention in which DNA can be chemically manipulated before being inserted in a nanochannel for optical mapping.

Referring to FIG. 1, per the present invention, DNA 10 can be initially processed in a solution 12 without being affixed to a surface such as may interfere with some chemical reactions. For example, a DNA 10 can be dyed with a fluorescent marker, such as YOYO-1 fluorescent dye (hereinafter, "YOYO-1").

Figures 3A, 3B, 3C:
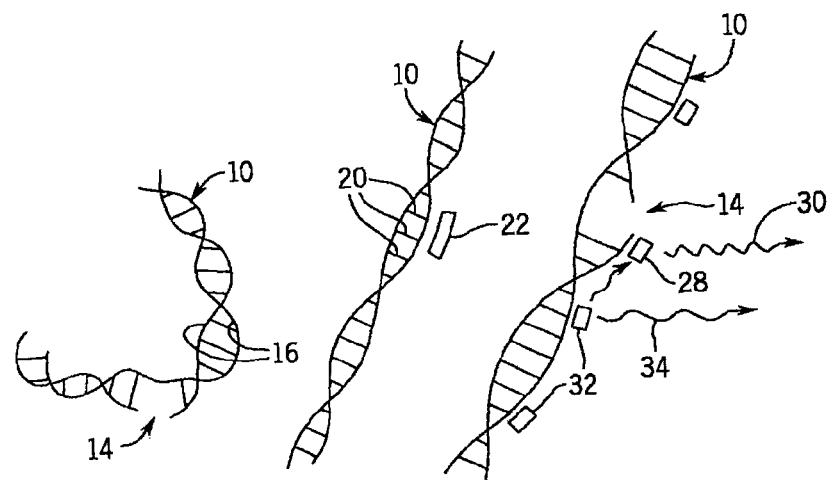
FIGS. 3a, 3b and 3c are simplified representations of DNA during three stages of the present invention in which the DNA is repaired, nicked, elongated, labeled and entrapped within a nanochannel.
Figure 4:
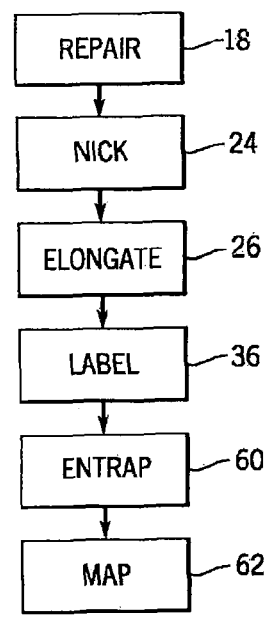
FIG. 4 is a flow chart showing these principle steps of the present invention.

Referring also to FIGS. 3a and 4, DNA 10 in solution, however, may include a number of inherent or pre-existing nicks 14 in which one strand 16 is broken. Such nicks 14 may result from damage from mechanical damage, UV light, or temperature.

In a first step, as represented by process block 18 of FIG. 4, incidental inherent nicks 14 are repaired to prevent confusion with nicks made for marking purposes. That is, DNA ligase and dideoxy nucleotides are added to the DNA 10 in solution to remove the inherent nicks. In addition, or alternative, a nuclease-free DNA polymerase (such as DNase-free DNA Polymerase I, available from Roche Applied Science) and dideoxy nucleotides are added to the DNA 10 in solution.

As shown in FIG. 3b, and represented by process block 24 of FIG. 4, the suspended DNA 10, as repaired, can be nicked at predefined base pair sequences 20 by enzyme 22. For example, the enzyme 22 can be a genetically engineered nicking endonuclease that cleaves only a single strand of a double-stranded polynucleotide, such as an enzyme of this class commercially available from New England Biolabs, including Nb.BbvCI and others. Typically, 20 units of Nb.BbvCI and deoxynucleotides are allowed to incubate with DNA 10 in solution at 37° C. As indicated by FIG. 3c, and represented by process block 36, the nicks 14 produced by enzyme 22 can be labeled by incorporating at the nicked site at least one fluorochrome 28 labeled deoxynucleotide providing a given frequency of light emission 30, and the remaining body of the DNA 10 can be labeled with a second fluorochrome 32 having a second frequency of emission 34. Fluorochrome 28 can be uniquely keyed to the point of the nick 14 whereas the fluorochromes 32 can distribute themselves uniformly over the remaining surface of the DNA 10. The nicked, labeled DNA can thus be imaged using Fluorescence Resonance Energy Transfer. These labeled nicks, when identified in position, will reveal characteristic sequence properties of the DNA 10.

Per process block 26 of FIG. 4, salt then can be removed from the DNA 10 by adjustment of the buffering solution 12 to cause an elongation of the DNA 10 and a corresponding increased rigidity.

The elongated and labeled DNA in solution may then be removed for example, by a pipette 38 and transferred into a first chamber 40 of a nanochannel assembly 42. The first chamber 40 provides one electrode 44 of an electrophoresis device and communicates through a set of nanochannels 50 with a second chamber 46 of the assembly 42 having a second electrode 51 of the electrophoresis device. As will be understood in the art, operation of a voltage across electrodes 44 and 51 will draw charged molecules such as DNA 10 from first chamber 40 to second chamber 46 through the nanochannels 50 extending therebetween. This step entraps the DNA within the nanochannels 50 for analyses or subsequent processing, as represented by process block 60 of FIG. 4.

Figure 2:
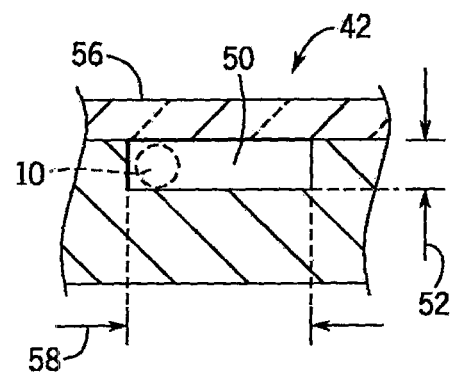
FIG. 2 is a cross-sectional view along line 2-2 of FIG. 1 through a nanochannel having nano- and micro-scale features.

Referring to FIG. 2, each nanochannel 50 may have a height 52 on the order of 30 nanometers effectively constraining the DNA 10 from substantial curvature in a vertical plane based on the cross-sectional diameter of the DNA 10. This constraint ensures that the DNA is maintained within the focal plane of a microscope objective which may view the DNA 10 through a transparent top wall 56 of the nanochannels 50.

The width of the channel 58 can be on the order of 1,000 nanometers (one micrometer) or less. This allows for simple fabrication of the channel using elastomeric molding techniques, for example, and improves the ability to draw the DNA into the nanochannels 50. The increased stiffness of the DNA 10 preserves its orientation and alignment in the nanochannels 50 despite the width of the nanochannels 50.

The DNA 10 may then be characterized or manipulated in other ways within the nanochannels 50 per process block 62. One wall of the nanochannels 50 can be semi-permeable to perform reactions on or otherwise affect the DNA 10, for example, restoring salt to the DNA.

Upon exit from the nanochannel, characterized molecules can be sorted or selected on the basis of user-specified parameters, as described. For example, the molecules can be sorted onto an array on the basis of chromosomal heritage (i.e., only DNA from a particular chromosome or set of chromosomes can be retained, if desired, by providing appropriate capture ligands. Alternatively, related sequences of, e.g., DNA encoding closely related genes can be retained with each capture ligand retaining a single unique version of the gene. Similarly, members of a single gene family can be sorted away from other related or unrelated genes. Also, molecules evidencing known aberrations or mutations can be sorted for further analysis. It will be apparent that the sorting possibilities are extensive.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

As used herein, persistence length refers to basic mechanical property quantifying the stiffness of a macromolecule of a polymer, reflecting the relative directional orientation of several infinitesimal segments. Under common laboratory conditions, DNA molecules have a persistence length of ~50 nm.

Example 1: Construction of Nanochannel Devices

Fabrication of nanochannel devices followed standard soft lithography techniques known to one skilled in the art. Whitesides G, et al., "Soft lithography in biology and biochemistry," Annu. Rev. Biomed. Eng. 3:335-373 (2001). To begin, a chrome mask, created with e-beam lithography at the University of Wisconsin Center for nanotechnology, was used as a mask in photolithography on negative photoresist spin-coated onto silicon wafers, creating an array of 1 μm channels. The wafer was etched to a depth of 100 nm by $CF_4$ gas. Photoresist was lifted off by piranha solution. The height of the pattern was determined by an alpha step profilometer and the width of the pattern was measured under scanning electron microscope. After fabrication of the nanochannels, a microchannel array was overlaid on the nanopatterned wafer. SU-8 2005 photoresist was used to create channels 5 μm high and 100 μm wide. FIG. 5 shows the nanochannels (diagonal lines; 100 nm high×1 μm wide) overlaid with microchannels (horizontal lines; 3 μm high× 100 μm wide).

Next, the devices were formed by molding polydimethylsiloxane (PDMS; Dow Corning; Midland, Mich.) onto the wafer described above. PDMS replicas were formed by curing the PDMS for 24 hours at 65° C. A short curing time (i.e. less than 24 hours), is not enough to make stable, PDMS nanochannel devices. An $O_2$ plasma treatment ($O_2$ pressure of ~0.67 millibars; load coil power 100 W; 36 seconds; Technics Plasma GMBH 440; Florence, Ky.) of the PDMS nanochannel devices was used to render the devices hydrophilic. Plasma-treated devices were stored in ultrapure water for twenty-four hours, as PDMS surfaces are reactive right after plasma treatment. Long-time storage in pure water makes the surfaces less reactive. In addition, the PDMS nanochannel devices were washed with 0.5 M EDTA (pH 8.5) three times to extract platinum ions, which was a catalyst for PDMS polymerization. Finally, the PDMS nanochannel devices were mounted on acid cleaned glass, prepared as described previously. Dimalanta E, et al., "A microfluidic system for large DNA molecule arrays," Anal. Chem. 76:5293-5301 (2004).

Example 2: Sequence-Specific Labeling of Nicked DNA

Sequence-specific labeled DNA was the result of the following steps: (1) linearization, (2) ligation, (3) nick site blocking, (4) nick translation, and (5) protein digestion. Linearization is required only when using circular DNA. Regardless of whether linearization was required, DNA ligase was used to remove inherent nicks in DNA. A DNA ligase reaction with T4 DNA ligase was performed at room temperature overnight. An overnight reaction ensures that ligation is complete and kills DNA ligase activity. To further ensure that and all inherent nicks were removed, DNA polymerase I (10 units) was added with dideoxy nucleotides (ddNTPs; 0.2 µM each) for 30 minutes at 37° C. ddNTPs incorporated into nicks block additional polymerase reaction and avoid random labeling. A nicking enzyme (Nb.BbvCI, 20 units; GC^ATGAGG) was then added with deoxynucleotides (dNTPs), such as ALEXA FLUOR 647-aha-dCTP fluorescent marker (2 µM), ALEXA FLUOR 647-aha-dUTP fluorescent marker (2 µM), dATP (20 µM), dCTP (1 µM), dGTP (20 µM) and dTTP (1 µM). Because DNA polymerase was added previously, no additional DNA polymerase was added during nick translation. The nick translation reaction was performed for 30 minutes at 37° C. EDTA (pH 8.0, 20 µM) was added to quench reactions. Proteinase K (100 ng/µl) and lauroyl sarcosine (0.1% w/v) were added to remove all enzymes.

Following sequence-specific labeling, DNA was counter-stained with YOYO-1 (25 µM; Molecular Probes; Eugene, Oreg.). DNA base pairs to YOYO-1 in a ratio of 6:1 for λ DNA and a ratio of 5:1 to T4 DNA. Final DNA samples containing DNA (1 ng/µl of λ DNA or 0.78 ng/µl of T4 DNA), Tris-EDTA buffer (pH 8.0), β-mercaptoethanol and POP6 (0.1% w/v; Applied Biosystems; Foster City, Calif.) were then loaded into the microchannels by capillary action and subsequently entered the nanochannels by application of an electric field. Tris-EDTA buffer concentration varied from 1×TE (10 mM Tris and 1 mM EDTA) to 0.01×TE (100 µM Tris and 10 µM EDTA). The ionic strength of the buffer can be varied both before or after entry into the nanochannels to affect elongation of the DNA.

An argon ion laser-illuminated inverted ZEISS 135M microscope was used to image DNA molecules. The microscope was equipped with a 63×ZEISS Plan-Neofluar oil immersion objective, a DAGE SIT68GL low-light level video camera connected to a SONY monitor for visual inspection of DNA molecules, and a charge-couple device (CCD) camera for acquiring focus and high-resolution images. A LUDL ELECTRONICS x-y stage and focus motor with 0.1-m resolution was used for x-y-z translation. Two emission filters were installed in the microscope, YOYO-1 emission filter XF3086 and ALEXA FLUOR 647 emission filter. The YOYO-1 filter was used to take images of DNA backbones; whereas the ALEXA FLUOR 647 filter was used to take fluorescence resonance energy transfer (FRET) images.

Example 3: Elongation of Labeled DNA

Figure 6A:
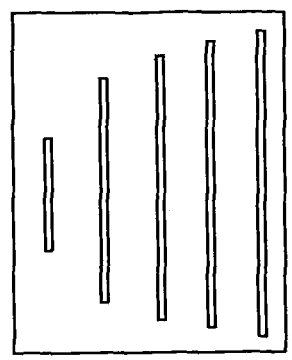
FIGS. 6a and b show the effect of buffer ionic strength on DNA elongation.
Figure 6B:
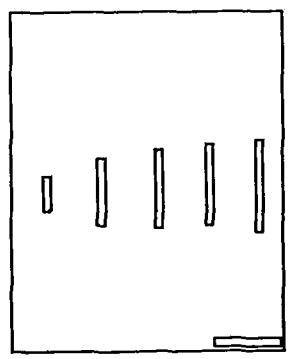

As shown in FIGS. 6a and 6b, diminished ionic strength buffer conditions increased intrachain electrostatic repulsion of DNA in the nanochannels, thereby increasing persistence length. Specifically, FIGS. 6a and 6b show typical images of T4 DNA (166 kbp; polymer contour length, 74.5 µm) and λ DNA (48.5 kbp; polymer length, 21.8 µm) elongated within nanochannels under low ionic strength buffer conditions (0.05×TE and 0.01×TE) showing apparent lengths of 40.9±8.4 µm (T4 DNA) and 13.0±2.4 µm (λ DNA).

Figure 7:
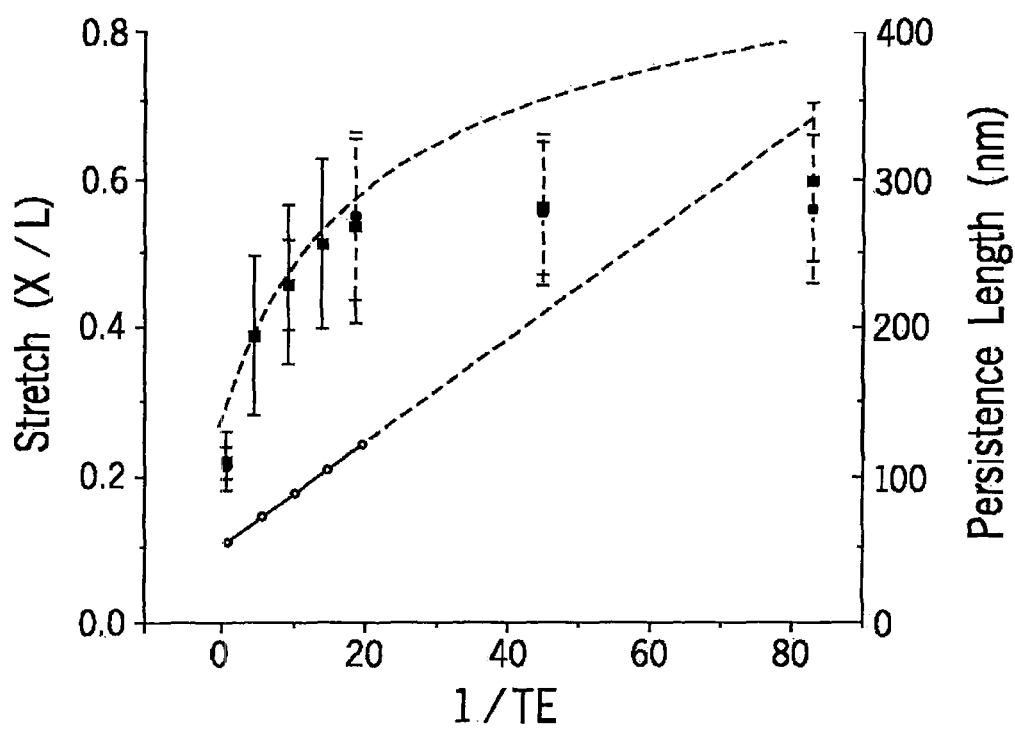
FIG. 7 graphically depicts the impact of buffer dilution upon DNA elongation.

As shown in FIG. 7, DNA elongation is a function of the dilution of TE (1/TE) reported as "stretch," and defined as the average apparent length, X, divided by the dye adjusted polymer contour length, L (e.g., L=21.8 for λ DNA); a stretch value of 1.0 indicates complete elongation. FIG. 7 also shows that the degree of DNA elongation is size independent and inversely related to salt concentration or ionic strength used for the calculation of persistence by the following equation:

$$P = P_o + P_{el} = P_o + 1/(4\kappa^2 l_b) = P_o + 0.324 I^{-1} \text{ Å};$$

where $P_o$ is the non-electrostatic intrinsic persistence length due to base stacking, $P_{el}$ is the electrostatic persistence length due to intrachain repulsion, $\kappa^{-1}$ is the Debye-Hückel screening length, and $l_b$ is the Bjerrum length (7 Å in water).

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method of preparing a double-stranded DNA molecule for optical analysis, the method comprising the steps of:
    ligating the DNA molecule to remove inherent nicks;
    nicking at least one predefined sequence position of one strand of the DNA molecule without breaking the double-stranded DNA molecule into wholly separate pieces, wherein at least one nicked position defines a pattern-characteristic of the nucleotide sequence of the DNA molecule;
    elongating the DNA molecule in a buffer having an ionic strength sufficiently low to increase the persistence length of the DNA molecule;
    labeling the DNA molecule with at least one fluorescent label wherein the fluorescent label is specific to the nicked position; and
    introducing the elongated and labeled DNA molecule suspended in the buffer into a channel to maintain the elongated and labeled DNA molecule in an elongated state capable of being analyzed optically without fixation to the channel.

2. The method of claim 1, wherein the ionic strength of the buffer is adjusted after the elongated DNA is introduced into the channel.

3. The method of claim 1, wherein the DNA molecule adopts an elongated form having a persistence length greater than 50 nm.

4. The method of claim 1, further comprising:
    detecting by optical analysis using a microscope at least one nicked position in the labeled DNA molecule maintained in an elongated state, whereby the analyzed elongated and labeled DNA molecule is capable of being sorted from a plurality of DNA molecules on the basis of the pattern characteristic of the nucleotide sequence defined by the at least one nicked position.

5. A method of providing an elongated and labeled DNA molecule in a channel for optical analysis, the method comprising:

(a) providing the DNA molecule in a buffer having an ionic strength sufficiently low that the molecule adopts an elongated form;
(b) labeling the DNA molecule with at least one fluorescent label; and
(c) introducing the elongated and labeled DNA molecule provided in the buffer into a channel having a cross-sectional dimension that constrains the elongated and labeled DNA which is at least as wide as the elongated and labeled DNA molecule and is less than 1000 nanometers, whereby the elongated DNA is constrained in the channel in the focal plane of a microscope objective, and wherein the elongated DNA molecule remains in the elongated state suitable for being analyzed optically without fixation to the channel.

6. The method of claim 5, further comprising adjusting the ionic strength of the buffer in which the elongated and labeled DNA is provided after the elongated and labeled DNA is introduced into the channel.

7. The method of claim 5, wherein the elongated DNA has a persistence length greater than 50 nm.

8. The method of claim 5, further comprising
(d) detecting by optical analysis using a microscope at least one nicked position in the elongated and labeled DNA molecule in the channel, whereby the analyzed elongated and labeled DNA molecule is capable of being sorted from a plurality of DNA molecules on the basis of the pattern characteristic of the nucleotide sequence of the DNA molecule that is defined by the at least one nicked position.

* * * * *